United States Patent [19]

Rosenau et al.

[11] Patent Number: 5,767,290
[45] Date of Patent: Jun. 16, 1998

[54] PREPARATION OF PROTECTED AMINES OR ALKYLATED AMINO ACIDS

[75] Inventors: Thomas Rosenau, Eisenach; Wolf-Dieter Habicher, Dresden, both of Germany; Chen-Loung Chen, Raleigh, N.C.

[73] Assignee: BASF Aktiengesellschaft, Ludwigshafen, Germany

[21] Appl. No.: 805,987

[22] Filed: Feb. 26, 1997

Related U.S. Application Data

[62] Division of Ser. No. 566,700, Dec. 4, 1995, Pat. No. 5,684,132.

[51] Int. Cl.$^6$ .................................................. C07D 311/04
[52] U.S. Cl. .................. 549/214; 548/311.4; 548/454; 548/525; 549/404; 549/405; 549/406; 549/408; 549/409; 549/410
[58] Field of Search ..................... 549/214, 404, 549/405, 406, 408, 409, 410; 548/311.4, 454, 525

[56] References Cited

FOREIGN PATENT DOCUMENTS 0159018  10/1995  European Pat. Off. .

OTHER PUBLICATIONS

Greene et al., Protective Groups in Organic Synthesis, 2nd Ed., New York, 1991.
Organic Reactions, vol. 4, pp. 174–255, 1948.
Rosenau et al., Tetrahedron, vol. 51, No. 29, pp. 7919–7926, 1995.
Rosenau et al., J. of Org. Chem., vol. 60, No. 25, pp. 8120–8121, 1995.
Baldwin et al., Chemical Abstracts, vol. 104, abstract 95446, 1986.
Nakamura et al., Chemical Abstracts, vol. 76, abstract 34055, 1972.
Boguth et al., Chemical Abstracts, vol. 75, abstract 4083, 1971.
Skinner et al., Chemical Abstracts, vol. 75, abstarct 18227, 1971.

Primary Examiner—Richard L. Raymond
Attorney, Agent, or Firm—Keil & Weinkauf

[57] ABSTRACT

The present invention relates to a process for preparing protected amines or amino acids. The invention furthermore relates to the use of tocopheryl radicals or radicals derived therefrom as protective groups for amines and amino acids, and to compounds obtained in this process as intermediates and to processes for preparing dipeptides and oligopeptides.

4 Claims, No Drawings

5,767,290

PREPARATION OF PROTECTED AMINES OR ALKYLATED AMINO ACIDS

This is a divisional of application Ser. No. 08/566,700, filed Dec. 4, 1995 now U.S. Pat. No. 5,684,132.

The present invention relates to a process for preparing protected amines or amino acids. The invention furthermore relates to the use of tocopheryl radicals or radicals derived therefrom as protective groups for amines and amino acids, and to compounds obtained in this process as intermediates and to processes for preparing dipeptides and oligopeptides.

The alkylation of primary amines normally leads to a mixture of amines which are alkylated more than once, as far as the corresponding quaternary ammonium compound. One method for preparing monoalkylated amines is therefore the elaborate reductive amination of aldehydes or reductive alkylation of amines. However, these frequently result in byproducts, or the yield is too low, especially with short-chain amines (review article: Org. Reactions, 4 (1948), 174–255). Another possibility is to prevent multiple alkylation of primary amines by protective groups. The known protective groups such as Boc and Fmoc (tert-butoxycarbonyl and fluorenylmethoxycarbonyl) are, however, frequently inadequate or unsatisfactory in their reactivity, ie. in respect of the conditions for the reaction with the compound to be protected, and the elimination of the protective group and the yields. A review of protective group chemistry is given in Greene T. W., Wats P. G. M., Protective Groups in Organic Synthesis, 2nd ed., Wiley, New York, 1991.

It is an object of the present invention to find compounds whose use as protective groups permits exclusive monoalkylation in the alkylation of amines and amino acids and, furthermore, which can be readily introduced and eliminated under selective reaction conditions and can be separated from the reaction mixture.

We have found that this object is achieved by the use of compounds of the formula I

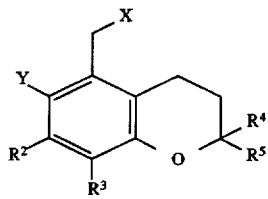

where

Y is —O—$R^1$ or —$NR^1{}_2$, where $R^1$ is H or $C_1$–$C_6$-alkyl and, in the case where Y=O, $R^1$ is also —Si($C_1$–$C_3$-alkyl)$_3$ or

with $R^6$=$C_1$–$C_3$-alkyl, $R^2$ and $R^3$ are each, independently of one another, H, $C_1$–$C_3$-alkyl, —O—$R^6$, —O-aryl or aryl, with $R^6$=$C_1$–$C_3$-alkyl, $R^4$ and $R^5$ are each, independently of one another, $C_1$–$C_{20}$-alkyl, aryl, $C_1$–$C_3$-alkyl-aryl, —CO—$R^7$ or —$CO_2R^7$ where $R^7$=H or $C_1$–$C_{20}$-alkyl, and X is Cl, Br, —$OSO_3R^o$ with $R^o$=$C_1$–$C_6$-alkyl, aryl, $C_1$–$C_3$-alkyl-aryl or $C_1$–$C_3$-alkylene-aryl for introducing protective groups of the formula II

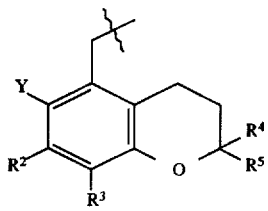

where

Y and $R^2$ to $R^5$ have the abovementioned meanings, into amines or amino acids.

The invention furthermore relates to a process for preparing secondary amines or monoalkylated amino acids by alkylation of primary amines or amino acids, wherein a radical of the above-mentioned formula II is used as protective group in the alkylation.

Besides the preparation of secondary amines, N-monoalkylated amino acids and the synthesis of di- and oligopeptides, compounds of the formula I can be used as advantageous amino protective groups in all processes which require protection of primary amino groups. The following conditions should be avoided:

a) presence of oxidizing agents, b) temperatures above 50° C., c) strongly basic medium in aprotic solvents, d) basic medium in protic solvents.

These reactions may cover the entire range of organic chemistry, and the use of the particular protective group reagent must be governed by the requirements of the relevant amine or other reagents used. Thus, for example, an O-protected tocopherol derivative is to be used in processes which require the absence of protons.

Compounds of the formula I can likewise be used to protect secondary amines, linear and cyclic, in a similar way to the protection of primary amines. The products obtained by the above processes are tertiary amines or N-dialkylated amino acids. Besides the preparation of tertiary amines and N-dialkylated amino acids, compounds of type I can likewise be used as advantageous amino protective groups in all processes which require protection of secondary amino groups. The following conditions should be avoided:

a) presence of oxidizing agents, b) temperatures above 50° C., c) strongly basic medium in aprotic solvents, d) basic medium in protic solvents.

These reactions may cover the entire range of organic chemistry, and the use of the particular protective group reagent must be governed by the requirements of the relevant amine or other reagents used. Thus, for example, an O-protected tocopherol derivative is to be used in processes which require the absence of protons. The processes indicated for primary amines or amino acids are employed unchanged to attach the Toc protective group to secondary amines and to eliminate the Toc protective group from secondary amines after completion of the reaction requiring N protection. Secondary amines have slightly higher reactivity than primary amines towards the protective group reagents of type I, which is evident in a beneficial way from the shorter reaction times for introducing the protective group.

A particular embodiment of the use and of this process is one wherein in formula I Y is —O—$R^1$ with $R^1$ H, $C_1$–$C_6$-alkyl, —Si($C_1$–$C_3$-alkyl)$_3$ or

with $R^6$=$C_1$–$C_3$-alkyl, $R^2$ and $R^3$ are each, independently of one another, H or $C_1$–$C_3$-alkyl, $R^4$ and $R^5$ are each, independently of one another, $C_1$–$C_{20}$-alkyl, aryl, $C_1$–$C_3$-alkyl-aryl, —COR$^7$ or —CO$_2$R$^7$, with R$^7$=H, $C_1$–$C_6$-alkyl, and X is Cl, Br.

It is particularly preferred when $R^1$ to $R^5$ have the following meanings:

$R^1$=H, —CH$_3$ or

SiMe$_3$
$R^2$, $R^3$ and $R^4$=—CH$_3$
X=Br
$R^5$=

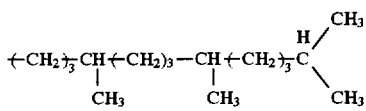

Another particular embodiment of the process comprises introducing, before the alkylation, a protective group of the formula II as set forth in claim 1 into the primary amine or into the amino acid, by reacting the primary amine with a compound of the formula I as set forth in claim 1 at from –40° C. to +100° C., in particular from –30° C. to +70° C., and eliminating it again after the alkylation.

Compounds of the formula I are disclosed in Tetrahedron, 51, No. 29 (1995), 7919–7926.

In the preferred form, the process according to the invention is carried out in the following way:

A primary amine of the formula III

     III where
$R^8$ can have the following meanings:
saturated or unsaturated $C_1$–$C_{14}$-alkyl, where the alkyl radical can be straight-chain or branched and be substituted by —NO$_2$, —CN, —OR$^6$, —C$_6$H$_5$, naphthyl, —CO$_2$R$^9$ or —F,
—C$_6$H$_5$, naphthyl, $C_3$–$C_8$-cycloalkyl or a $C_5$–$C_7$-heterocycle with one or 2N, O and/or S atoms, where these radicals can be substituted by —NO$_2$, —CN, —OR$^6$, —R$^5$, —CO$_2$R$^7$ or —F,
or a radical

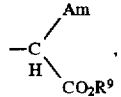

where Am is a radical of a type such that the corresponding compound of the formula III represents all natural D- and/or L-amino acids which are unmodified or modified with $C_1$–$C_4$-alkyl radicals, and $R^9$ is H or $C_1$–$C_6$-alkyl, is reacted with a compound of the formula I as set forth in claim 1 at from –40° C. to +100° C. to give the ammonium compound of the formula IV

     IV where T is the protective group of the formula II as set forth in claim 1, the compound of the formula IV is then converted with a base into the compound of the formula V

     V the compound of the formula V is subsequently reacted with an alkylating agent $R^{10}A^\ominus$ to give the compound of the formula VI or VIa

     VI

     VIa where $R^{10}$ is $C_1$–$C_{12}$-alkyl, $C_1$–$C_3$-alkyl-aryl, $C_1$–$C_{12}$-hydroxyalkyl, benzyl, $C_4$–$C_7$-cycloalkyl, $C_2$–$C_{12}$-alkenyl, $C_2$–$C_{12}$-alkynyl and $A^\ominus$ is the counter ion resulting from the alkylating agent, and finally the compound VII

     VII is obtained from the compound of the formula VI or VIa after eliminating the radical T.

The invention furthermore relates to compounds of the formulae IV, V, VI and VIa indicated above.

The invention additionally relates to the use of compounds of the formula V with $R^8$ meaning

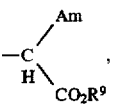

where Am and $R^9$ have the abovementioned meanings, in the preparation of peptides.

In the case where the radicals $R^1$ to $R^5$ in the protective group of the abovementioned formula II have the following meanings $R^1$=

—SiMe$_3$
$R^2$, $R^3$ and $R^4$=—CH$_3$
$R^5$=

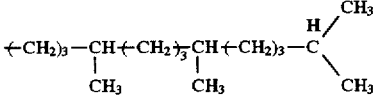

this protective group is referred to hereinafter as the tocopheryl radical or, for short, as "Toc" and is represented by the following formula IX

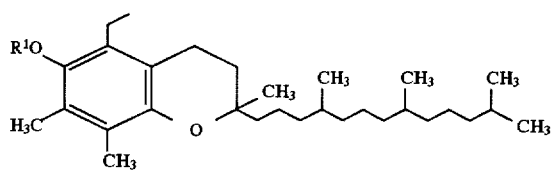

A preferred embodiment of the process according to the invention for preparing secondary amines can be represented by the following Reaction Scheme I:

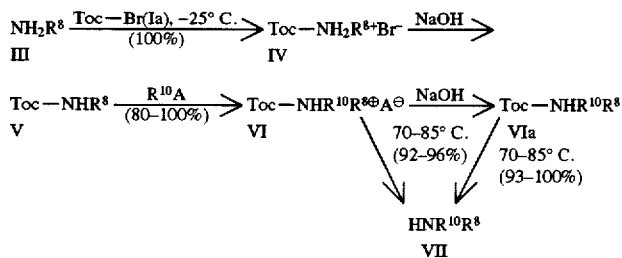

A particularly preferred compound according to the invention, which is obtained as intermediate IV in the process according to the invention, has the following formula VIII

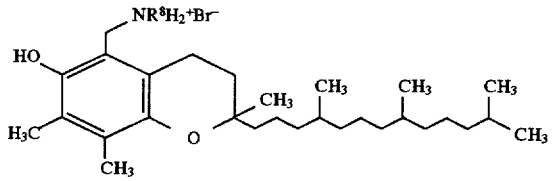

As is evident from the above scheme, it is also possible after the alkylation initially to prepare the intermediate VIa, by reacting the initially produced ammonium compound VI with a base, and then to obtain the secondary amine VII.

The use according to the invention of compounds of the formula V in the preparation of peptides can be represented in a preferred embodiment by the following Reaction Scheme 2:

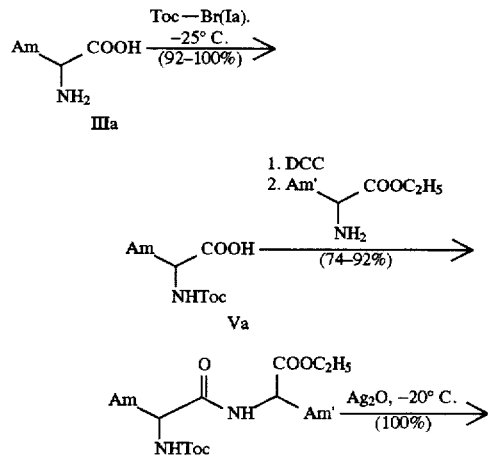

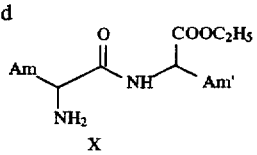

Coupling of compound V (identified by Va in Scheme 2) to another amino acid or ester thereof (represented by the radical Am' in the scheme) is carried out in a conventional way using dicyclohexylcarbodiimide (DCC). The resulting dipeptide X can be reacted in a similar way to give a tripeptide and further to give a tetrapeptide and so on.

The particular advantage of the present invention is that it provides a protective group which is orthogonal to previous protective groups. A compound of the formula I particularly used for introducing the protective group is, moreover, easily obtainable because it can be prepared from commercially available α-tocopherol (vitamin E). In addition, the Toc protective group can be eliminated by changing the temperature, there being formation, via an ortho-quinone methide, of the spiro dimer of α-tocopherol, which can easily be removed. Concerning the formation of the ortho-quinone methide and the dimer, reference is made to Tetrahedron, 51, No. 29, (1995) 7919–7926.

The present invention can preferably be carried out in the following specific manner:

The primary amine $NR^8H_2$ is converted by 5a-bromo-α-tocopherol (Toc-Br) (Ia) into the corresponding tocopheryl ammonium bromide IV. Double alkylation of the amine with Ia as the alkylating agent was not observed, not even if a large excess of Toc-Br was applied. This can be attributed to the bulky shape of the protective group with its $C_{16}$-side chain. After liberation of the tocopheryl-protected amine (Toc-$NR^8H$) V, alkylation is carried out with a slight excess of alkyl halide $R^{10}A$. Again, the bulky tocopherol moiety prevents dialkylations, even in the presence of excessive alkyl halide. The products, dialkyl tocopheryl ammonium salts (Toc-$NR^{10}R^8H^+A^{\ominus}$) VI, were obtained nearly quantitatively.

The introduction of the group II is carried out below 0° C. in nonpolar and polar aprotic solvents (e.g. dichloromethane, ethyl ether, n-hexane, petroleum ether, dioxane or THF). Several ways exist for the removal of the protecting group, resulting in the desired secondary amines ($HNR^{10}R^8$) VII. All methods for the removal of the 5a-α-tocopheryl moiety are based on the ready formation of the orto-quinone methide intermediate upon elimination of the amino "subhstituent" at position 5a of the tocopherol. This intermediate undergoes consecutive reactions: in aprotic media, the spiro-dimer of α-tocopherol is formed quantitatively; in protic media, a mixture of the dimer and α-tocopheryl quinone is obtained. No other by-products were observed upon removal of the Toc group under the prevailing conditions. In general, removal of the group II can be achieved by heating the ammonium salt VI, or the corresponding dialkyl tocopheryl amine VIa to 70° C., either as a pure substance or in a solvent.

Other possibilities for the removal of the Toc group include the treatment of VI or VIa with mild oxidants, preferably $Ag_2O$, at lower temperatures in organic solvents or with bases in aqueous media.

The mildest and most widely applicable procedure for the removal of the 5a-tocopheryl group is its oxidative cleavage. For this purpose, the dialkyl tocopheryl ammonium salts are suspended in n-hexane or dichloromethane (50 ml) and stirred with 2 mmol freshly prepared $Ag_2O$ for 30 min at −20° to 0° C. $AgNO_3$ or $AgBr$ can also be used instead of $Ag_2O$. After separation of the solids, the secondary amines can be obtained.

If heat treatment or oxidative cleavage as a means for the removal of the Toc group is not feasible, then the dialkyl tocopheryl ammonium halides can be stirred rapidly with a mixture of concentrated KOH (10 ml) and diethyl ether (50 ml) for 10 min at 0° C. or at room temperature. After phase separation, the aqueous phase is extracted twice with 20 ml of diethyl ether. The desired secondary amines can be reextracted from the combined ethereal phases with 2N HCl.

Several methods to remove the amino-protecting group are available, so that the choice can adapt to the needs for special reaction conditions set by the respective amines or other protecting groups employed. In all cases, the hydrophilicity of the secondary amines produced can be utilized to separate them in extraction processes from the strongly hydrophobic products of the cleaved protecting group. The separation of the secondary amines as the corresponding ammonium salts is an even more convenient procedure. The amines finally obtained are very pure, making further purification unnecessary in the majority of cases.

Compounds of formula I are also valuable reagents for the protection of amino functions in amino acids. The reaction of 5a-bromo-α-tocopherol (Ia) with the amino group of amino acids can be interpreted as a special case of the above-described procedure, since amino acids with unsubstituted $NH_2$ groups can be regarded as primary amines. The corresponding N-Toc amino acids are prepared in the same fashion as the tocopheryl protected primary amines, giving also quantitative yields. In case of secondary amino functions in addition to the primary amine in a molecule, it is possible that all primary and secondary amino functions in the molecule are protected by groups of formula II, utilizing the significantly different reactivities of Toc-protected primary amines as compared to Toc-protected secondary amines.

N-alkylation of the N-Toc amino acids with alkyl halides, followed by the removal of the amino-protecting group, results in high yields of N-alkyl amino acids. This procedure resembles the sequence presented in Reaction Scheme 1.

N-alkylation of amino acids is less common in synthetic organic chemistry than the coupling of amino acids to di- or oligopeptides. 5a-Bromo-α-tocopherol (Ia) as an aminoprotecting group also shows promising behavior in this field. Results were obtained from the synthesis of dipeptides X according to the well known DCC-method. ((Sheehan, J. C.; Hess, G. P. J. Am. Chem. Soc. 1955, 77, 1067. Marglin, A.; Merrifield, R. B. Ann. Rev. Biochem., 1970, 39, 841. Bodansky, M.; Bodansky, A. in the Practice of Peptide Synthesis; 2nd rev. ed., Springer Verlag: Berlin, N.Y., 1994) employing amino acids Va that had been protected by 5a-bromo-α-tocopherol. The reaction sequence is shown in Scheme 2. The reactions presented in Scheme 2 were also carried out using O-methyl-5a-bromo-α-tocopherol. This compound, as well as O-trimethylsylyl-5a-bromo-α-tocopherol, can be substituted for 5a-bromo-α-tocopherol when its sensitivity towards oxidants or the presence of the acidic proton of the phenolic OH group causes problems because of special requirements of the amine or other coreactants employed. The overall yield of the reaction sequence is determined exclusively by the coupling reaction between the N-Toc-protected and the carboxyl-protected amino acid, since both introduction and removal of the protecting group from the N-Toc protected dipeptide are quantitative or nearly-quantitative steps.

The same experimental procedure as described for primary amines applies for introduction and removal of the Toc group in the amino acid chemistry.

The bulky shape of 5a-bromo-α-tocopherol as an aminoprotecting group is responsible for the prevention of dialkylations mentioned above. In addition, special molecular characteristics of the Toc-group, namely the presence of a chroman-6-ol system and an isoprenoid side chain, bring about the beneficial features of its easy oxidative removal and good separability. The OH group of 5a-bromo-α-tocopherol (Ia) and of the Toc group in protected primary amines or amino acids is hardly amenable to O-alkylation, ensuring that in Reaction Scheme 1 only the nitrogen, not the oxygen of the protective group, is alkylated. On the other hand, the OH group in Toc is readily oxidized, due to the vitamin E character of the compound.

The group according to formula II is stable to a wide range of reaction and work-up conditions: it is inert to mild or even harsh acidic conditions, Lewis acids, and hydrogenations and is also stable to mild bases, e.g., commonly applied basic auxiliaries, such as DBU, pyridine, triethylamine or N-ethyldiisopropylamine. In addition, the conditions required for the removal of the protecting group II are selective and mild enough to tolerate the widest range of complementary protecting groups. Therefore, it might well serve in different orthogonal sets of protecting groups.

Numerous common protecting groups, e.g., Bn, Boc, Z and Fmoc, are normally installed using their halide derivatives in the presence of auxiliary bases. The group II proved to be stable under these conditions. On the other hand, the very mild conditions used to attach compound I to amines do not impair any of those groups.

Removal of protecting groups under acidic conditions (e.g., Boc, Z), with Lewis acids (e.g., Boc) or by hydrogenolysis (e.g., Bn, Z, Fmoc) do not interfere with tocopheryl-protected structures present. Basic conditions for the cleavage of a protecting group (e.g. Fmoc) are only safe as long as mild bases in aprotic media are used (e.g., pyridine, triethylamine in DMF). Strong bases in aqueous media, however, lead to deprotonation and immediate cleavage of the Toc group.

The removal of the protecting group II at slightly elevated temperatures is especially useful in the presence of other protecting groups, since auxiliaries that might interfere with those groups are not added. The other option for the removal of the protecting group II, its oxidative cleavage with $Ag_2O$, is an especially mild procedure and suitable for instance, to avoid formation of piperazinediones, as shown for the deprotection of N-Toc protected amino acids and dipeptides. Moreover, since there are only few protecting groups that are oxidatively cleaved, the vast majority of other protecting groups remains unaffected upon removal of Toc by means of silver salts. Only the para-methoxy-benzyl (PMB) and related protecting groups are usually removed by means of oxidation. Under the conditions used for their removal, the Toc group is also cleaved. Deprotection of N-Toc amines by $Ag_2O$, however, leaves PMB and derived groups unchanged.

The advantages of compound I for introducing an amino-protecting group shall be briefly summarized. First of all, the ease of introduction and removal of the protecting group and the unambiguous course of these processes are to be mentioned. Both steps proceed in high yields under mild conditions in the absence of any further auxiliaries, merely by changing the reaction temperature. These facts ensure a broad applicability of the process, even if labile compounds are involved. In contrast to the majority of other amino-protecting groups, the protecting group II does not require awkward or sophisticated preparative techniques for its attachment to or its removal from the amino function. The group II can be selectively and efficiently removed under highly specific conditions using either the protected amine or its corresponding ammonium salt. The products of the cleaved protecting group are easily separable from the reaction mixture. In addition, the amines obtained can be very conveniently separated via their ammonium salts.

EXAMPLES

All reagent and glassware must be completely dry. Since 5a-bromo-α-tocopherol, a vitamin E derivative, is sensitive toward oxygen, it should be stored under nitrogen in a cold place. Most amines are much more stable to air and light if they are converted into their ammonium salts. Therefore, if an amine or N-Toc protected amine is not to be used immediately, it can be stored in salt form.

1. Preparation of N-butylethyl amine by ethylation of Toc-protected butyl amine with ethyl bromide.

Example 1

In a 250 ml flask equipped with magnetic stirrer, dropping funnel and gas inlet, 1.000 mmol butyl amine was dissolved in dichloromethane (50 ml) and cooled to $-25°$ C. in an inert atmosphere. At the same temperature, a precooled solution of 1.000 mmol (0.510 g) 5a-bromo-α-tocopherol in dichloromethane (25 ml) was added dropwise while stirring. The solution became immediately cloudy, after approximately 5 min white crystals started to precipitate. The solution was stirred for an additional 30 min at $-20°$ C., and the precipitated white solid was removed by filtration under inert atmosphere and washed twice with 10 ml of the solvent applied above. The tocopheryl butyl ammonium bromides obtained are infinitely stable in a dry, dark place below $10°$ C. under inert gas.

A 100 ml flask was charged with the obtained ammonium bromide, 50 ml of dichloromethane, and 0.1 mol (4.100 g) of dry, coarse-grained NaOH. The mixture was stirred vigorously for 10 min at $-20°$ C. under exclusion of oxygen and the solids were carefully removed. The solution of the tocopheryl-protected butyl amine did not contain impurities in detectable amounts and was used without further purification in all cases Yield: 95%.

(If the solubility of the amines is too low, the release of these amines can be carried out in aqueous solution: to a slurry of the obtained ammonium salt in dichloromethane (50 ml), 50 ml of 0.1M aqueous NaOH can be added and the mixture is stirred for 1 min at $-10°$ to $0°$ C. under exclusion of oxygen. The organic phase is separated, washed with 10 ml of ice-cold water and dried over $MgSO_4$.)

1.1 mmol of the obtained ethyl bromide was added dropwise to the solution of the N-protected amine at room temperature. The solution was stirred until no further precipitate was formed, usually 30 min. The ethyl butyl tocopheryl ammonium halide, obtained as a white solid, was removed, washed thoroughly with a total of 20 ml dichloromethane and dried under vacuum.

(The alkyl halide can be used in large excess if necessary, since a solid product is obtained which can be easily separated. However, the use of 1.1 mol of alkyl halide per mole of amine is sufficient. No improvements in yield, only shorter reaction times, were achieved if larger amounts of alkyl halide were used. Dialkylation of the tocopheryl-protected amine was not observed. Even if a tenfold excess of alkyl halide was applied to the dialkyl tocopheryl amine or its ammonium salt under the prevailing conditions, only traces of quaternary compounds were detected, proving the quality of the tocopheryl moiety in preventing dialkylation.)

The obtained ammonium salts were warmed at $10°$ C./min to $70°$ C. for 1 h or to $85°$ C. for 10 min. The heat treatment was carried out in the absence of oxygen. The dry ethyl butyl tocopheryl ammonium halide was used.

(However, a suspension of the salt in an appropriate solvent is more suitable, especially in the case of smaller charges. The solvent used (e.g. n-hexane, toluene) should be an excellent solvent for either the free amine or the products of the cleaved protecting group, the latter case being preferred).

The crystalline precipitate slowly disappeared during the process of heat treatment. The color of the solvent employed changed from colorless to bright yellow due to the formation of the spiro-dimer of α-tocopherol. Pulverized, dry NaOH was present during the period of heating. the temperature was lowered to $50°$ C. (At only slightly higher temperatures ($70°$ C. to $85°$), addition of any auxiliary can be avoided.) The resulting secondary amine was extracted with 2N HCl or separated by filtration after conversion into the corresponding ammonium salts by dry, gaseous HCl.

In general:

Another mild procedure for the removal of the 5a-tocopheryl group is its oxidative cleavage. For this purpose, the dialkyl tocopheryl ammonium salts are suspended in n-hexane or dichloromethane (50 ml) and stirred with 2 mmol of freshly prepared $Ag_2O$ for 30 min at temperatures between $-20°$ and $0°$ C. $AgNO_3$ or AgBr can also be used instead of $Ag_2O$. While the reaction temperature seems to have only minor effects on the rate of the cleavage, the quality of the silver oxide used is crucial. Only freshly prepared $Ag_2O$ without traces of water was used. After separation of the solids, the secondary amines are obtained as described above.

If the heat treatment for the removal of the Toc group is not feasible for any reason, or $Ag_2O$ is too strong an oxidant for the compound being used, the dialkyl tocopheryl ammonium salts are stirred rapidly for 10 min with a mixture of 10 ml concentrated KOH and 50 mL diethyl ether at $0°$ C. or room temperature. The phases are separated, and the aqueous phase is extracted twice with 20 ml of diethyl ether. The desired secondary amines can be re-extracted from the combined ethereal phases with 2N HCl. However, methods avoiding aqueous media seem to be more suitable.

According to this procedure the following products were obtained (examples 2–15), see Table 1.

2. Preparation of N-monoalkylated amino acids by alkylation of N-Toc protected amino acids with alkyl halides.

The above experimental procedure was applied to amino acids. The starting material, an amino acid with a free $NH_2$ group, corresponds to the primary amine. The products are N-monoalkylated amino acids, corresponding to the above obtained secondary amines.

According to this procedure the following products were obtained (examples 16–19), see Table 1.

TABLE 1

| Nr. | Primary amine | Alkylating agent | Product | Overall yield |
|---|---|---|---|---|
| 1 | butylamine | ethyl bromide | N-butylethylamine | 95% |
| 2 | tert-butylamine | cyclohexyl chloride | N-tert-butylcyclohexylamine | 89% |
| 3 | cyclohexylamine | tert-butyl chloride | N-tert-butylcyclohexylamine | 70% |
| 4 | cyclopentylamine | allyl bromide | N-allylcyclopentylamine | 90% |
| 5 | octylamine | octyl chloride | di-n-octylamine | 98% |
| 6 | ethylamine | ethyl chloride | diethylamine | 98% |
| 7 | allylamine | allyl chloride | diallylamine | 85% |
| 8 | benzylamine | benzyl chloride | dibenzylamine | 91% |
| 9 | aniline | ethyl bromide | N-ethylphenylamine | 96% |
| 10 | aniline | benzyl chloride | N-benzylphenylamine | 96% |
| 11 | aniline | 2-chloroethanol | 2-anilinoethanol | 96% |
| 12 | 1-naphthylamine | ethyl iodide | N-ethylnaphthylamine | 84% |
| 13 | benzylamine | methyl iodide | N-benzylmethylamine | 92% |
| 14 | 2-aminopyridine | methyl iodide | 2-(methylamino)pyridine | 93% |
| 15 | aniline | chloroacetic acid | N-phenylglycine | 94% |
| 16 | alanine | ethyl iodide | N-ethylalanine | 96% |
| 17 | leucine | benzyl chloride | N-benzylleucine | 92% |
| 18 | 2-aminoisobutyric acid | methyl iodide | 2-(methylamino)isobutyric acid | 98% |
| 19 | glutamic acid | benzyl bromide | 2-(benzylamino)glutamic acid | 93% |

3. Preparation of dipeptides by DCC coupling of N-Toc amino acids and amino acid ethyl esters.

The coupling of two amino acids, one of them N-Toc protected, with dicyclohexylcarbodiimide (DCC) as shown in Reaction Scheme 2 was carried out according to well-established standard procedures. Ethyl esters were used as carboxyl protected amino acids; N-protection was achieved using the presented protecting group. The afore mentioned procedure applies without alterations to a) the introduction of the Toc group to the amino acid as starting material, and b) the removal of the Toc group from the dipeptides formed as products.

According to this procedure the following products were obtained (examples 20–25), see Table 2

TABLE 2

| Nr. | Product | N-Toc protected amino acid | Overall yield |
|---|---|---|---|
| 20 | Ala-Ala | N-toc-Ala | 96% |
| 21 | Ala-Cys | N-toc-Ala | 90% |
| 22 | Cys-Cys | N-toc-Cys | 68% |
| 23 | Gly-Gly | N-toc-Gly | 92% |
| 24 | Leu-Ala | N-toc-Leu | 93% |
| 25 | Leu-Leu | N-toc-Leu | 93% |

The compounds obtained according to the examples have been identified by the following analytical methods:

$^1$H NMR spectra were recorded at 300 MHz, $^{13}$C NMR spectra at 80 MHz (Bruker AC-300P) in $CDCl_3$ with TMS as the internal standard. Chemical shifts are expressed in $\delta$ value. GCMS was performed on a Hewlett Packard (5890 Series II, 30 m DBWAX column, EI, 70 eV, ITD). MS (FAB$^+$) was carried out on a Jeol HX1-10 in a m-nitrobenzyl alcohol matrix.

1. Secondary Amines by Alkylation of N-Toc Protected Primary Amines, Followed by Removal of the Protecting Group (Compare to Reaction Scheme 1).

N-Butylethylamine (alkylation of N-toc-butylamine with ethyl bromide).

Anal. calcd. for $C_6H_{15}N$: C, 71.22; H, 14.94; N, 13.84. Found: C, 71.24; H, 14.98; N, 13.80%.

$^{13}$C NMR ($CDCl_3$): $\delta$ 14.05, 15.40, 20.60, 32.45, 44.25, 49.65.

N-tert.-Butylcyclohexylamine (a) alkylation of N-toc-tert.-butylamine with cyclohexyl chloride).
Anal. calcd. for $C_{10}H_{21}N$: C, 77.35; H, 13.63; N, 9.02. Found: C, 77.32; H, 13.71; N, 8.97%.
$^{13}$C NMR ($CDCl_3$): $\delta$ 25.75, 25.90, 30.10, 37.10, 50.90, 51.20.

(b) alkylation of N-toc-cyclohexylamine with tert.-butyl chloride:
Anal. calcd. for $C_{10}H_{21}N$: C, 77.35; H, 13.63; N, 9.02. Found: C, 77.40; H, 13.65; N, 9.00%.
$^{13}$C NMR ($CDCl_3$): $\delta$ 25.75, 25.90, 30.10, 37.10, 50.90, 51.20.

N-Allylcyclopentylamine (alkylation of N-toc-cyclopentylamine with allyl bromide).
Anal. calcd. for $C_8H_{15}N$: C, 76.74; H, 12.07; N, 11.19. Found: C, 76.70; H, 12.128; N, 11.25%.
$^{13}$C NMR ($CDCl_3$): $\delta$ 24.10, 33.20, 51.35, 59.30, 115.45, 137.20.

Di-n-octylamine (alkylation of N-toc-n-octylamine with n-octyl chloride).
Anal. calcd. for $C_{16}H_{35}N$: C, 79.59; H, 14.61; N, 5.80. Found: C, 79.61; H, 14.65; N, 5.83%.
$^{13}$C NMR ($CDCl_3$): $\delta$ 14.85, 23.50, 30.10, 30.40, 31.10, 32.65, 51.00

Diethylamine (alkylation of N-toc-ethylamine with ethyl chloride).
Purity determined by GC.
$^{13}$C NMR ($CDCl_3$): $\delta$ 15.40, 44.05.

Diallylamine (alkylation of N-toc-allylamine with allyl chloride).
Anal. calcd. for $C_6H_{11}N$: C, 7.17; H, 11.41; N, 14.42. Found: C, 74.21; H, 11.34; N, 14.43%.
$^{13}$C NMR ($CDCl_3$): $\delta$ 51.80, 115.75, 136.80.

Dibenzylamine (alkylation of N-toc-benzylamine with benzyl chloride).
Anal. calcd. for $C_{14}H_{15}N$: C, 85.24; H, 7.66; N, 7.10. Found: C, 85.38; H, 7.72; N, 7.01%
$^{13}$C NMR ($CDCl_3$): $\delta$ 53.10, 126.80, 128.00, 128.30, 140.25.

N-Ethylaniline (alkylation of N-toc-aniline with ethyl bromide).

Anal. calcd. for $C_8H_{11}N$: C, 79.29; H, 9.15; N, 11.56. Found: C, 79.21; H, 9.18; N, 11.60%.

$^{13}C$ NMR (CDCl$_3$): δ 14.85, 38.40, 112.65, 117.10, 129.10, 148.25.

N-Benzylaniline (alkylation of N-toc-aniline with benzyl chloride).

Anal. calcd. for $C_{13}H_{13}N$: C, 85.21; H, 7.15; N, 7.64. Found: C, 85.29; H, 7.24; N, 7.61%.

$^{13}C$ NMR (CDCl$_3$): δ 53.85, 112.75, 117.25, 126.80, 128.10, 128.30, 129.10, 140.65, 148.85.

N-Phenylethanolamine (2-Anilinoethanol) (alkylation of N-tocaniline with 2-chloroethanol).

Anal. calcd. for $C_8H_{11}NO$: C, 70.04; H, 8.08; N, 10.21. Found: C, 70.11; H, 8.03; N, 10.23%.

$^{13}C$ NMR (CDCl$_3$): δ 46.05, 61.05, 113.20, 117.85, 129.25, 148.05.

N-Ethyl-1-naphthylamine (alkylation of N-toc-1-naphthylamine with ethyl iodide).

Anal. calcd. for $C_{12}H_{13}N$: C, 84.17; H, 7.65; N, 8.18. Found: C, 84.07; H, 7.71; N, 8.22%.

$^{13}C$ NMR (CDCl$_3$): δ 14.70, 38.60, 104.15, 117.05, 119.70, 123.25, 124.45, 125.55, 126.55, 128.55, 134.20, 143.50.

N-Benzylmethylamine (alkylation of N-toc-benzylamine with methyl iodide).

Anal. calcd. for $C_8H_{11}N$: C, 79.29; H, 9.15; N, 11.56. Found: C, 79.298; H, 9.17; N, 11.54%.

$^{13}C$ NMR (CDCl$_3$): δ 36.05, 56.10, 126.85, 128.05, 128.30, 140.20.

2-(Methylamino)pyridine (alkylation of N-toc-2-aminopyridine with methyl iodide).

Anal. calcd. for $C_6H_8N_2$: C, 66.64; H, 7.46; N, 25.90. Found: C, 66.70; H, 7.51; N, 25.81%.

$^{13}C$ NMR (CDCl$_3$): δ 29.00, 106.10, 112.50, 137.30, 148.05, 159.60.

N-Phenylglycine (alkylation of N-toc-aniline with chloroacetic acid).

Anal. calcd. for $C_8H_9NO_2$: C, 63.56; H, 6.00; N, 9.27. Found: C, 63.58; H, 5.94; N, 9.27%.

$^{13}C$ NMR (CDCl$_3$)CD$_3$COOD): δ 44.90, 112.20, 116.55, 128.75, 147.70, 172.50.

N-Ethylalanine (alkylation of N-toc-alanine with ethyl iodide).

Anal. calcd. for $C_5H_{11}NO_2$: C, 51.26; H, 9.46; N, 11.96. Found: C, 51.21; H, 9.53; N, 12.01%

$^{13}C$ NMR (CDCl$_3$/CD$_3$COOD): δ 15.50, 17.30, 40.15, 49.75, 175.45.

N-Benzylleucine (alkylation of N-toc-leucine with benzyl chloride).

Anal. calcd. for $C_{13}H_{19}NO_2$: C, 70.56; H, 8.65; N, 6.33. Found: C. 70.61; H, 8.64; N, 6.32%

$^{13}C$ NMR (CDCl$_3$/CD$_3$COOD): δ 22.95, 25.85, 41.30, 53.55, 63.10, 126.80, 128.30, 140.35, 177.35.

2-(methylamino)isobutyric acid (alkylation of N-toc-2-aminoisobutyric acid with methyl iodide).

Anal. calcd. for $C_5H_{11}NO_2$: C, 51.26; H, 9.46; N, 11.96. Found: c, 51.21; H, 9.55; N, 11.92%.

$^{13}C$ NMR (CDCl$_3$/CD$_3$COOD): δ 24.00, 30.40, 65.90, 179.60.

2-(Benzylamino)glutamic acid (alkylation of N-toc-glutamic acid with benzyl bromide).

Anal. calcd. for $C_{12}H_{15}NO_4$: C, 60.75; H, 6.37; N, 5.90. Found: C, 60.79; H, 6.43; N, 5.99%

$^{13}C$ NMR (CDCl$_3$/CD$_3$/COOD): δ 26.45, 31.15, 52.55, 64.95, 126.60, 128.00, 128.30, 140.85, 171.15, 172.45.

2. Dipeptides by DCC-coupling of N-Toc Protected Amino Acids and Amino Acid Ethyl Esters, Followed by Removal of the Amino-protecting Group (Compare to Reaction Scheme 2).

Alanylalanine ethyl ester (coupling of N-toc-alanine with alanine ethyl ester).

Anal. clcd. for $C_8H_{16}N_2O_3$: C, 51.05; H, 8.57; N, 14.88. Found: C, 51.06; H, 8.61; N, 14.97%

MS: 188.2 [M$^+$].

Alanylcysteine ethyl ester (coupling of N-toc-alanine with cysteine ethyl ester).

Anal. calcd. for $C_8H_{16}N_2O_3S$: C, 43.62; H, 7.32; N, 12.72; S, 14.55. Found: C, 43.66; H, 7.44; N, 12.75; S, 14.62%.

MS: 220.3 [M$^+$].

Cysteinylcysteine ethyl ester (coupling of N-toc-cysteine with cysteine ethyl ester).

Anal. calcd. for $C_8H_{16}N_2O_3S_2$: C, 38.08; H, 6.39; N, 11.10; S, 25.41. Found: C, 38.02; H, 6.47; N, 11.18; S, 25.34%.

MS: 252.3 [M$^+$].

Glycylglycine ethyl ester (coupling of N-toc-glycine with glycine ethyl ester).

Purity determined by GC and TLC.

MS: 160.2 [M$^+$].

Leucylalanine ethyl ester (coupling of N-toc-leucine with alanine ethyl ester).

Anal. calcd. for $C_{11}H_{22}N_2O_3$: C, 57.37; H, 9.63; N, 12.16. Found: C, 57.45; H, 9.75; N, 12.23%.

MS: 230.1 [M$^+$].

Leucylleucine ethyl ester (alkylation of N-toc-leucine with leucine ethyl ester).

Anal. calcd. for $C_{14}H_{28}N_2O_3$: C, 61.37; H, 10.36; N, 10.28. Found: C, 61.33; H, 10.50; N, 10.24%.

MS: 272.4 [M$^+$].

3. Two Examples of intermediates IV (N-Toc Protected Primary Amines)

The numbering of the carbon atoms in tocopherols and the nomenclature proposed by the IUPAC (IUPAC-IUB Commission on Biochemical Nomenclature (CBN) Arch. Biochim. Biophys., 1974, 165, 1, and IUPAC-IUB Nomenclature of Tocopherols and Related Compounds. Eur. J. Biochim., 1982, 123, 473) have been used, as shown in the following figure for α-tocopherol

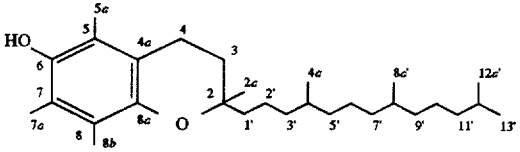

The δ-values of the atoms of the isoprenoid side chain (C-1' to C-13') are only very slightly affected by modifications of the chroman structure (Urano, S.; Matsuo, M. Chem. Pharm. Bull., 1980, 28 (7), 1992, and Brownstein; S.; Ingold, K. U. J. Org. Chem., 1989, 54 (3), 561–569). The signals of aliphatic moieties attached to the tocopherol part are covered by the resonances of the side chain in the majority of cases.

N-Toc-ethylamine (3,4-Dihydro-5-ethylaminomethyl-2,7,8-trimethyl-2-(4,8,12-trimethyltridecyl)-2H-1-benzopyran-6-ol, N-5a-α-tocopherylethylamine.

Anal. calcd. for $C_{31}H_{55}NO_2$: C, 78.59; H, 11.70; N, 2.96. Found: C, 78.62; H, 11.77; N, 3.01%.

$^1$H NMR (CDCl$_3$): δ 2.1 (3H, s, C$\underline{H}_3$, C-7a), 2.15 (3H, s, C$\underline{H}_3$, C-8b), 2.65 (2H, t, ArC$\underline{H}_2$CH$_2$, C-4), 3.55 (2H, q, N—C$\underline{H}$—CH$_3$), 4.70 (2H, s, Ar—C$\underline{H}_2$—N, C-5a), resonances of the isoprenoid side chain between 0.8 and 2.0 ppm.

$^{13}$C NMR (CDCl$_3$): δ 14.99 (N—CH$_2$—$\underline{C}$H$_3$), 19.54 (C-4a'), 19.59 (C-8a'), 19.98 (C-4), 20.98 (C-2'), 22.52 (C-13'), 22.61 (C-12a'), 23.61 (C-2a), 24.48 (C-6'), 24.80 (C-10'), 27.94 (C-12'), 31.51 (C-3), 32.65 (C-8'), 32.76 (C-4'), 37.30 (C-7'), 37.36 (C-5'), 37.46 (C-9'), 37.57 (C-3'), 39.39 (C-11'), 39.80 (C-1'), 65.93 (N—$\underline{C}$H$_2$—CH$_3$), 67.88 (C-5a), 74.15 (C-2), 114.89; 115.98; 122.97; 125.43 (C-4a; C-5; C-7; C-8), 155.48; 147.50 (C-6; C-8a).

N-Toc-allylamine (5-Allylaminomethyl-3,4-dihydro-2,7,8-trimethyl-2-(4,8-12-trimethyltridecyl)-2H-1-benzopyran-6-ol (N-5a-α-tocopherylallylamine).

Anal. calcd. for $C_{32}H_{55}NO_2$: C, 79.12; H, 11.41; N, 2.88. Found: C, 79.03; H, 11.48; N, 2.92%.

$^1$H NMR (CDCl$_3$): δ 2.1 (3H, s, C$\underline{H}_3$, C-7a), 2.15 (3H, S, C$\underline{H}_3$, C-8b), 2.60 (2H, t,ArC$\underline{H}_2$CH$_2$, C-4), 4.08 (2H, d, N—C$\underline{H}_2$—CH=CH$_2$), 4.71 (2H, s, CH$_2$, Ar—C$\underline{H}_2$—N, C-5a), 5.25 (1H, d$^2$, N—CH$_2$—CH=CH$_2$ [trans]), 5.35 (1H, d, N—CH$_2$—CH=C$\underline{H}_2$ [cis]), 5.9 (1H, m, N—CH$_2$—C$\underline{H}$=CH$_2$), resonances of the isoprenoid side chain between 0.8 and 2.0 ppm.

$^{13}$C NMR (CDCl$_3$): δ 19.58 (C-4a'), 19.60 (C-8a'), 19.93 (C-4), 21.02 (C-2'), 22.55 (C-13'), 22.63 (C-12a'), 23.63 (C-2a), 24.45 (C-6'), 24.80 (C-10'), 27.97 (C-12'), 31.49 (C-3), 32.65 (C-8'), 32.79 (C-4'), 37.31 (C-7'), 37.38 (C-5'), 37.47 (C-9'), 37.58 (C-3'), 39.40 (C-11'), 39.83 (C-1'), 67.07 (C-5a), 115.38; 116.00; 123.09; 125.79 (C-4a; C-5; C-7; C-8), 144.78; 147.45 (C-6; C-8a), allyl group: 71.08, 117.98, 133.83.

We claim:

1. A compound of the formula VIa

T—NR$^8$R$^{10}$       VIa and ammonium salts thereof of the formula VI

T—NHR$^8$R$^{10+}$A$^-$,       VI wherein

T is the protective group of the formula II

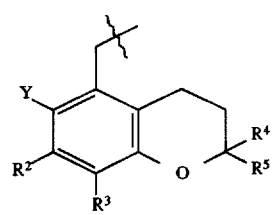
II wherein

Y is —O—R$^1$ or —NR$^1{}_2$, where

R$^1$ is H or C$_1$–C$_6$-alkyl and, in the case where Y=O—R$^1$, R$^1$ is also —Si(C$_1$–C$_3$-alkyl)$_3$ or

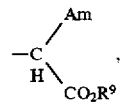

with R$^6$=C$_1$–C$_3$-alkyl

R$^2$ and R$^3$ are each, independently of one another, H, C$_1$–C$_3$-alkyl, —O—R$^6$, —O-aryl or aryl, with R$^6$=C$_1$–C$_3$-alkyl, R$^4$ and R$^5$ are each, independently of one another, C$_1$–C$_{20}$-alkyl, aryl, C$_1$–C$_3$-alkyl-aryl, —CO—R$^7$ or —CO$_2$R$^7$ with R$^7$=H or C$_1$–C$_{20}$-alkyl, and R$^8$ is —C$_6$H$_5$, naphthyl, C$_3$–C$_8$-cycloalkyl or a C$_5$–C$_7$-heterocycle with one or 2N, O and/or S atoms, where these radicals can be substituted by —NO$_2$, —CN, —OR$^6$, —R$^6$, —CO$_2$R$^9$ or —F, or a radical

where Am is a radical of a type such that the corresponding compound of the formula III

R$^8$—NH$_2$      III represents all natural D- and/or L-amino acids which are unmodified or modified with C$_1$–C$_4$-alkyl radicals, and R$^9$ is H or C$_1$–C$_6$-alkyl.

R$^{10}$ is H, C$_1$–C$_{12}$-alkyl, C$_1$–C$_3$-alkyl-aryl, C$_1$–C$_{12}$-hydroxylalkyl, benzyl, C$_4$–C$_7$-cycloalkyl, C$_2$–C$_{12}$-alkenyl, or C$_2$–C$_{12}$-alkynyl, and A$^-$ is a suitable counter ion.

2. The compounds of claim 1 wherein R$^{10}$ is H.
3. The compounds of claim 1 wherein A$^-$ is Cl$^-$ or Br$^-$.
4. The compounds of claim 2 wherein A$^-$ is Cl$^-$ or Br$^-$.

* * * * *